United States Patent [19]
Kawanabe et al.

[11] Patent Number: 5,452,619
[45] Date of Patent: Sep. 26, 1995

[54] METHOD FOR PIPETTING A BLOOD SAMPLE

[75] Inventors: Junichi Kawanabe; Masaaki Takeda; Hitomi Katagi; Yuko Kato, all of Mitaka, Japan; Gregory A. Bielarczyk, Lombard; Rosie L. Magee, Oak Park, both of Ill.

[73] Assignee: Abbott Laboratories, Abbott Park, Ill.

[21] Appl. No.: 211,382

[22] PCT Filed: Oct. 2, 1992

[86] PCT No.: PCT/JP92/01281

§ 371 Date: Jul. 5, 1994

§ 102(e) Date: Mar. 31, 1994

[87] PCT Pub. No.: WO93/07494

PCT Pub. Date: Apr. 15, 1993

[30] Foreign Application Priority Data

Oct. 4, 1991 [JP] Japan ................. 3-257642

[51] Int. Cl.$^6$ .................. G01N 33/49; G01N 1/28
[52] U.S. Cl. ................... 73/864.01; 73/863
[58] Field of Search ............. 73/864.01, 863, 73/863.21, 64.56

[56] References Cited

FOREIGN PATENT DOCUMENTS

| 19895 | 5/1980 | Japan. |
|---|---|---|
| 25314 | 6/1986 | Japan. |
| 11910 | 2/1989 | Japan. |

OTHER PUBLICATIONS

*Patent Abstracts of Japan* GAP PO85, vol. 5, No. 165 Abs Pub. Date (Oct. 22, 1981) "Extruding Device of Separated Sample" by Mitsugi Ichiki et al. (Abstract of 56–94238 dated Jul. 20, 1981).

*Patent Abstracts of Japan* Grp P148, vol. 6, No. 203 Abs Pub. date (Oct. 14, 1982) "Dispensing Method for Particle Sample" by Tokio Kanou et al. (abstract of 57–111451 dated Jul. 10, 1982).

*Primary Examiner*—Thomas P. Noland
*Attorney, Agent, or Firm*—Mark C. Bach

[57] ABSTRACT

In pipetting a blood plasma component and a red blood cell component separated vertically in a blood sample by a centrifugation, the red blood cell component having a high viscosity is aspirated as quickly as possible. A nozzle 32 is composed of a nozzle base 35 and a disposable tip 36, and is transferred upwardly and downwardly and to the right and left by an XYZ robot 34. At first the blood plasma component in the blood sample put in a test tube 62 is pipetted by a nozzle 32, and then an inner wall of the disposable tip 36 is coated with the blood plasma component, and thereafter the red blood component is pipetted.

4 Claims, 5 Drawing Sheets

BLOOD PLASMA ASPIRATION

RED BLOOD CELL DILUTED SOLUTION DISPENSATION

Fig. 10

BLOOD PLASMA AND RED BLOOD CELL PIPETTING

METHOD FOR PIPETTING A BLOOD SAMPLE

BACKGROUND OF THE INVENTION

Embodiments described herein relate to a method for pipetting a blood plasma component and a red blood cell component, etc. with blood analysis or blood test which is carried out in an automatic pipetting apparatus.

Figure 10:
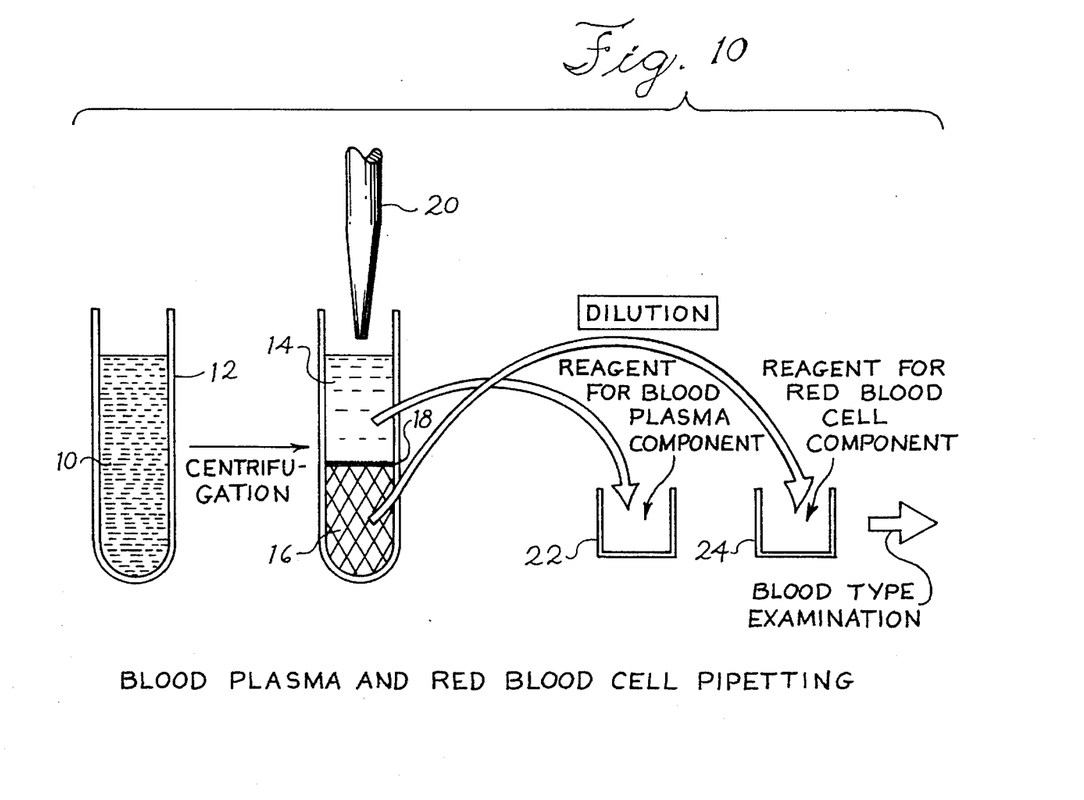
FIG. 10 is an explanatory view for showing an operation of pipetting the blood plasma and the red blood cells as a preprocess for a blood type test.

Various kinds of tests are conducted for a blood sample collected from a human body. For example, in a blood type test, as shown in FIG. 10, the collected blood sample 10 is put into a test tube 12 and is then separated into a blood plasma component 14 and a red blood cell component 16 by centrifugation. Practically, a small quantity of a white blood cell component 18 appears between the blood plasma component 14 and the red blood cell component 16. Since the white blood cell component is not relevant to the following description, it is omitted from the other drawings.

A well known method for pipetting a blood sample which is carried out in a conventional apparatus comprises mainly two steps: a step for pipetting blood plasma and a step for pipetting red blood cells. In the blood plasma pipetting step, the blood plasma 14 is aspirated by a nozzle tip 20 and is then separately piperred into a plurality of recipient containers 22 in a predetermined volume. In the red blood cell pipetting step, the red blood cell component 16 is aspirated by the same nozzle tip 20 and is then pipetted into a non-illustrated diluting container to be mixed with a diluent, whereupon the diluted solution of red blood cell component 16 is again aspirated by the nozzle tip 20 and is then pipetted into a plurality of another recipient containers 24, respectively in a predetermined volume.

Blood type testing reagents (a reagent for the blood plasma component, and a reagent for the red blood cell component) are introduced into the recipient containers 22, 24, respectively.

Then, these recipient containers 22, 24 are moved to an agglutination testing apparatus, where agglutination tests of the blood sample in the containers are conducted optically. From the results of these measurements, the blood types, such as A, B, O, AB and RH, of the blood sample are determined.

However, the red blood cell component is a high viscosity liquid (or a gel-like substance), so a quick pipetting of the red blood cell component cannot be achieved by the conventional pipetting method. Since the red blood cell component can not be aspirated smoothly through an orifice at a distal end of the nozzle tip due to high viscosity of the red blood cell component, it takes a long time until an amount of red blood cell component to be aspirated reaches to a predetermined volume. Consequently, a quick pipetting operation can not be conducted by using the conventional pipetting apparatus.

Further, in the conventional pipetting apparatus, contamination between blood samples has been prevented by thoroughly cleaning the nozzle tip for each sample, without exchanging the nozzle tip with a new one for each blood sample. Since such cleaning operation is labor-intensive and complex, it has been long desired to use a disposable nozzle tip.

SUMMARY OF THE INVENTION

It is therefore an object of the present invention to provide a blood sample pipetting method in which a high viscous red blood component can be aspirated as quickly as possible, thereby improving the processing ability of the pipetting apparatus.

A further object of the present invention is to provide a blood sample pipetting method in which the blood plasma component and the red blood cell component can be aspirated smoothly by a disposable nozzle tip.

According to the invention as defined in the claims, the aforementioned object of the present invention can be achieved by a method for pipetting a blood sample, wherein a blood plasma component and a red blood cell component vertically separated from each other in a test tube are sequentially pipetted into another recipient containers by a nozzle tip, comprising: a blood plasma component pipetting step of aspirating the blood plasma existing in an upper portion of the test tube, and transferring the blood plasma component into another recipient container by the nozzle tip; a red blood cell pipetting step of aspirating the red blood cell component existing in a lower portion of the test tube, and transferring the red blood cell component into another recipient container by the same nozzle tip; and the red blood cell pipetting step including a blood plasma coating step of coating an inner surface of the nozzle tip with the blood plasma component at least to such an extent in the nozzle tip that the red blood cell component to be subsequently aspirated reaches, prior to an aspiration of the red blood cell component.

According to the invention as defined in the claims, the aforementioned object of the present invention can be achieved by a method for pipetting a blood sample further including a coating preparing step of leaving a small quantity of the blood plasma component to be used for coating, within the nozzle tip at the end of the blood plasma pipetting step.

According to the invention as defined in the claims, the aforementioned object of the present invention can be achieved by a method for pipetting a blood sample, wherein the blood plasma coating step includes a positioning step of positioning the nozzle tip containing the remaining blood plasma component to be used for coating in an upper portion of the test tube from which the blood plasma component has been taken; a step of raising and lowering the blood plasma component, in which a coating blood plasma component is raised and lowered within the nozzle tip, thereby coating an inner surface of the nozzle tip therewith, while the nozzle tip being positioned in the upper portion of the test tube; and a blood plasma returning step of moving the nozzle tip downwardly and then returning (dispensing) the remaining blood plasma into the test tube.

According to the invention as defined in the claims, the aforementioned object of the present invention can be achieved by a method for pipetting a blood sample, wherein the nozzle tip is a disposable type, and the same nozzle tip is used continuously for a single blood sample through both the blood plasma pipetting step and the red blood cell pipetting step, and the nozzle tip is exchanged with a new one prior to pipetting of the next blood sample.

According to the invention as defined in the claims, since the inner surface of the nozzle tip is coated with the blood plasma component, it is possible to reduce the frictional resistance of the inner surface of the nozzle tip during aspiration of the blood cell component and to thereby aspirate the red blood cell component smoothly. Therefore, it is possible to reduce the time needed for aspirating the red blood cell component, and to improve the pipetting ability per unit time of a pipetting apparatus. If the inner surface of the nozzle tip is thus coated with the blood plasma component, it is possible to effectively prevent the red blood cell component from adhering (sticking) to the inner surface of the nozzle tip so that during dilution of the sample, a smooth (high-speed) stirring and an improvement of precision of dilution can be obtained. This coating is performed at least to such an extent that the red blood cell component to be subsequently aspirated reaches.

According to the invention as defined in the claims, since a part of the blood plasma component aspirated into the nozzle tip during the blood plasma pipetting step is used for coating the inner surface of the nozzle tip, it is unnecessary to aspirate an additional quantity of the blood plasma component only for coating, so that the coating step can be performed continuously from the blood plasma component pipetting step.

According to the invention as defined in the claims, since the blood plasma coating can be performed while the nozzle tip is positioned in an upper portion of the test tube from which the blood plasma has been aspirated, a different blood sample put in another test tube is avoided from being contaminated by the previous sample. Since the remaining blood plasma used for coating is returned into the test tube, it is possible to perform the blood plasma component coating, without wasting a valuable blood sample.

According to the invention as defined in the claims, it is possible to surely prevent blood sample contamination, without thoroughly cleaning the nozzle tip.

DETAILED DESCRIPTION OF THE PREFERRED EMBODIMENTS

One embodiment of the present invention will now be described with reference to the accompanying drawings.

Figure 1:
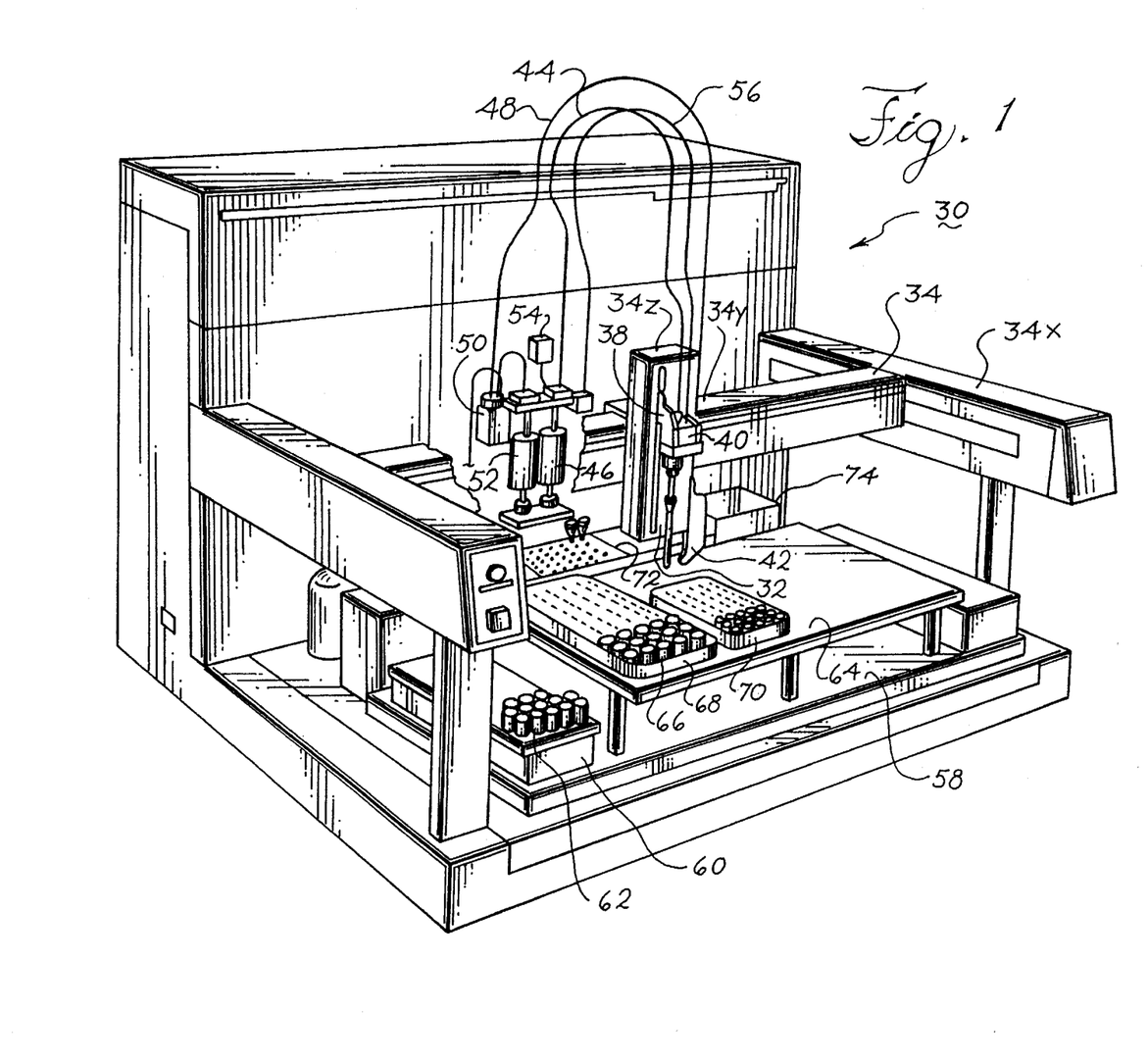
FIG. 1 is a perspective view of a pipetting apparatus employing a pipetting method of the present invention.

FIG. 1 shows a blood sample pipetting apparatus 30 (hereinafter called "apparatus") employing a blood sample pipetting method of the present invention. FIG. 1 is a perspective view of the apparatus 30.

In this embodiment, the apparatus 30 pipettes the blood plasma component and the red blood cell component after centrifugation to perform a preprocess for blood type test.

As shown substantially in the central portion of FIG. 1, a nozzle 32 for aspirating a blood sample is held by an XYZ robot 34 so as to be movable three-dimensionally.

Figure 2:
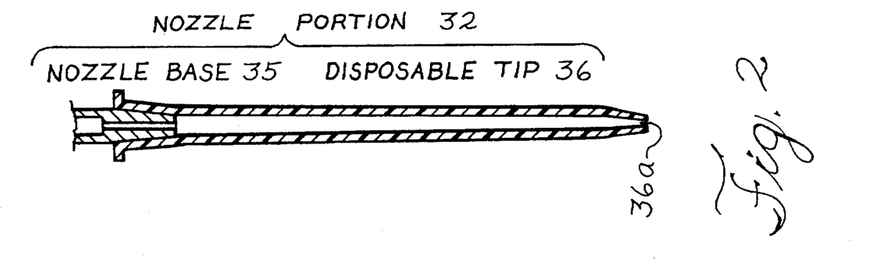
FIG. 2 is a cross-sectional view showing a main part of a nozzle.

FIG. 2 shows a cross sectional view of a main part of a nozzle 32. The nozzle 32 is composed of a nozzle base 35, and a disposable tip serving as a nozzle tip 36. Thus, the pipetting apparatus in the embodiment of the present invention uses a disposable type nozzle tip. A distal end of the nozzle base 35 is forced into an upper opening of the nozzle tip 36 and is fitted therein. Thus, the nozzle tip 36 is fixed firmly to the nozzle base 35. The nozzle tip 36 has at its lower end thereof an orifice 36a from which the blood sample is aspirated and dispensed. The nozzle tip 36 may be made of a hard plastic material or the like, and the nozzle base 35 may be made of a metal.

In FIG. 1, the XYZ robot 34 is composed of an X drive portion 34x, an Y drive portion 34y and a Z drive portion 34z. To the Z drive portion 34z, an elevator 38 provided with the nozzle 32 is connected so as to be vertically movable. The elevator 38 has a limit switch 40 serving as a jamming sensor or the like.

The limit switch 40 detects an external force imparted upwardly to the nozzle 32 and having a value greater than a predetermined force.

Onto the z drive portion 34z, a diluent pipette 42 for dispensing a diluent is fixedly mounted. An air hose 44 is connected at one end thereof to the nozzle 32 and at the other end thereof to a syringe 46 serving as a pump for causing aspirating and dispensing actions. A diluent hose 48 is connected at one end thereof to the diluent pipette 42 and at the other end thereof to a syringe 52 via an electromagnetic valve 50.

Between the syringe 46 and the nozzle 32, a pressure sensor 54 for measuring an internal pressure of the air hose 44 is connected. A signal from the limit switch 40 is sent to the apparatus via a cable 56.

On a test tube rack 60 placed on a pipetting table 58, a plurality of test tubes 62 containing blood samples which have been already subjected to a centrifugation treatment are held uprightly. Each test tube 62, as shown in FIG. 10, contains the blood sample in which the blood plasma component and the red blood cell component are separated in an upper portion and a lower portion of the test tube 62, respectively. On a horizontal table 64 mounted on the pipetting table 58, a dilution tray 68 provided with a plurality of diluting containers 66, and a microplate 70 are placed. On the microplate 70, a plurality of wells are placed for serving as a recipient container for containing the blood plasma component or diluted solution of the red blood cell component. After all of the blood samples have been pipetted, the microplate 70 is moved to a subsequent apparatus for blood type test, whereupon a agglutination test, for example, is made optically. The agglutination test may be made visually.

In the apparatus of the present invention, the nozzle tip is a disposable type and is exchanged successively with a new one. A plurality of new nozzle tips are prepared on a nozzle tip stand 72. There is also provided a nozzle scrap tray 74.

Therefore, in the apparatus of the present invention, it is possible that the blood plasma component or the red blood cell component is aspirated by the nozzle tip 36 of the nozzle 32 and is then transferred into another recipient container. The apparatus may also be applied to purposes other than pipetting of the blood sample. Various kinds of applications are possible.

Figure 3:
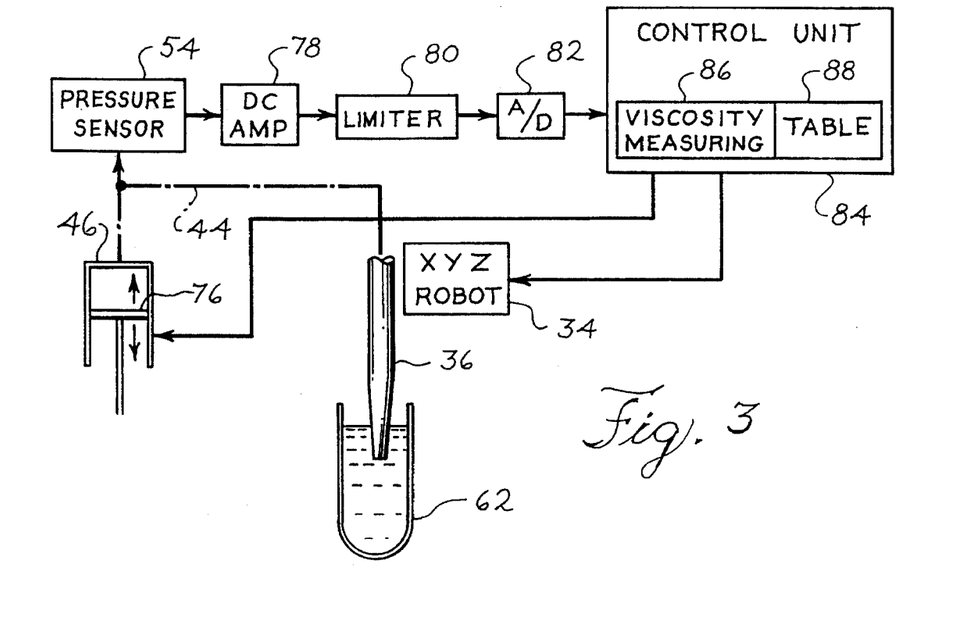
FIG. 3 is a block diagram of the pipetting apparatus of FIG. 1.

FIG. 3 is a block diagram of the apparatus of the embodiment of the present invention. By moving a piston 76 up and down, inside volume of the syringe 46 varies, so that an aspirating pressure or a dispensing pressure is transmitted to the nozzle tip 36 of the nozzle 32 via the air hose 44 to perform aspiration or dispensation of the blood sample. The internal pressure of the air hose 44 is detected by the pressure sensor 54, a sensor signal outputted from the pressure sensor 54 is amplified by a D.C. amplifier 78 and is then fed to an analog-digital converter 82 via a limiter circuit 80. The limiter circuit 80 is a protection circuit for suppressing any excessive input. The analog-digital converter 82 converts the sensor signal into a digital signal and feeds the digital signal to a control unit 84.

The control unit 84 includes a computer, for example, for controlling the inside volume of the syringe 46 and the XYZ robot 34, etc. In the embodiment, the control unit 84 also includes a viscosity measuring unit 86 and a table 88, both described below.

Embodiments of a pipetting method of the present invention, using the above-mentioned apparatus will now be described below.

Figure 4:
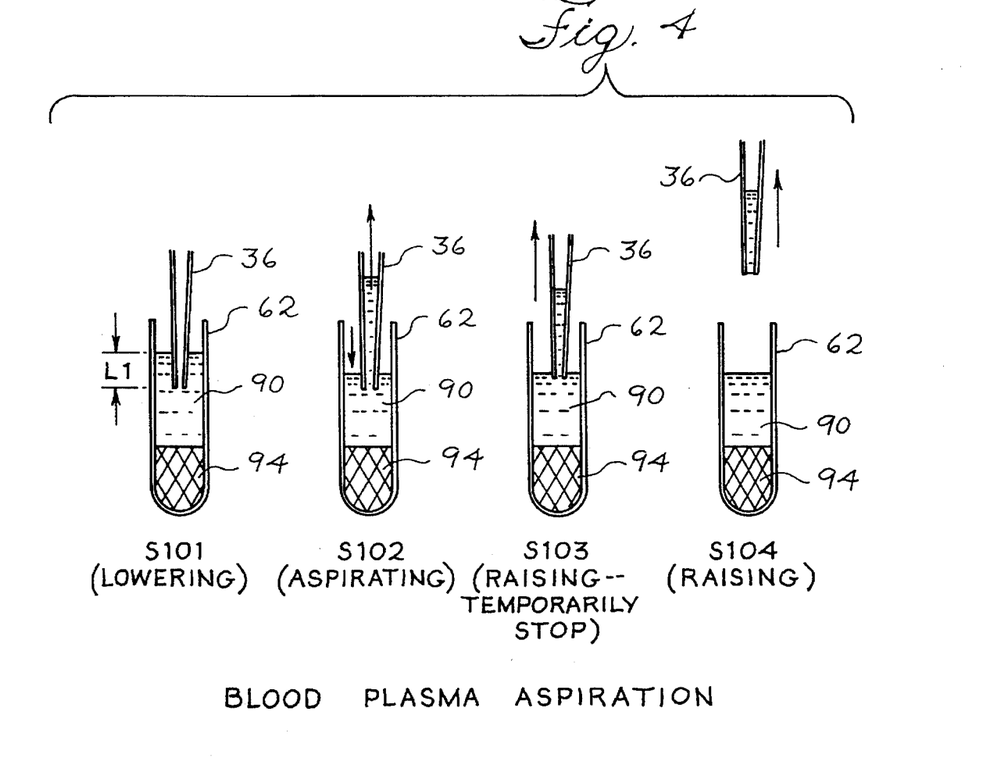
FIG. 4 is an explanatory view for showing a step, in which blood plasma is aspirated into the nozzle during a step of pipetting blood plasma.
Figure 5:
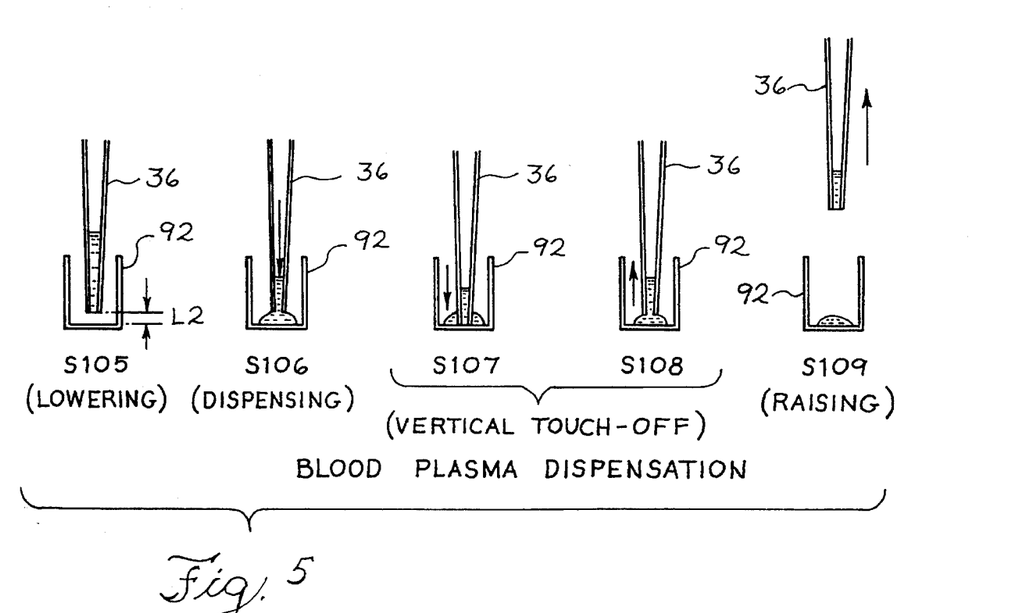
FIG. 5 is an explanatory view for showing a step, in which the blood plasma is dispensed from the nozzle during a step of pipetting the blood plasma.

FIGS. 4 and 5 show a blood plasma pipetting step. FIG. 4 shows a blood plasma component aspirating step, and FIG. 5 shows a blood plasma component dispensing step.

In FIG. 4, at step 101, the nozzle tip 36 is lowered from above the test tube 62 and is stopped so that the distal end of the nozzle tip 36 is inserted into the blood plasma component 90 to be positioned at a predetermined distance L1 downward from a blood surface. L1 is preferably 2 to 3 mm. If the distal end of the nozzle tip 36 is inserted too deeply into the blood plasma component 90, the two components once separated by the centrifugal method tend to be mixed again with each other.

When the nozzle tip 36 is lowered, the liquid surface is detected. This liquid surface detection is performed by monitoring the internal pressure of the hose 44 by the pressure sensor 54. When the internal pressure of the hose 44 is changed sharply, the control unit 84 confirms that the distal end of the nozzle tip 36 has reached the liquid surface.

At step 102, the blood plasma component 90 is aspirated. Specifically, the piston 76 is drawn to increase the inside volume of the syringe 46, whereby the blood plasma is taken in the nozzle tip 36. For example, about 30 to 300 µl of the blood plasma 90 is aspirated. As described in detail below, this aspirated amount of blood Plasma component includes a small amount of blood plasma component to be used for coating. Preferably, the amount of blood plasma component to be aspirated should be determined by taking account of the amount of blood plasma component that finally would attach onto an inner surface of the nozzle tip 36 and would not be dispensed from the nozzle tip 36.

At step 103, the nozzle tip 36 is raised and stopped temporarily just before the distal end of the nozzle tip 36 leaves from the surface of the blood plasma component 90. After a lapse of, for example, about 0.25 sec., the nozzle tip 36 is raised again at step 104. The reason why the step 103 is needed here in the present invention is that the blood plasma component attaching onto an outer surface of the nozzle tip 36 is returned into the test tube 62, thereby improving the precision of the pipetting. Next to step 104, step 105 of FIG. 5 is executed.

In the blood plasma dispensing step of FIG. 5, at step 105, the nozzle tip 36 is lowered into a predetermined well 92 and is stopped so that the distal end of the nozzle tip 36 is positioned at a distance L2 off the bottom of the well 92. In view of the characteristics of the blood, L2 is preferably about 2 mm. If the blood plasma component is dispensed from a too high position, it would become a so-called ball, so that it is difficult to transfer the blood plasma component into the well 92 quickly. Further, if the distal end of the nozzle tip 36 comes into contact with the bottom of the well 92, it becomes very difficult to dispense the blood plasma component.

At step 106, a part (predetermined amount) of the blood plasma component existing in the nozzle tip 36 is dispensed.

At step 107, the nozzle tip 36 is lowered until its distal end comes into slight contact with the bottom of the well 92. The contact condition can be monitored by the limit switch 40. At step 108, the nozzle tip 36 is raised. Thus, at step 107 and step 108, a so-called vertical touch-off system is employed, so that the blood plasma component attaching onto the inner surface of the nozzle tip 36 can be dispensed quickly.

At step 109, the nozzle tip 36 is raised to repeat the dispensing step (S105–S109) in another wells, and finally, a predetermined volume of blood plasma component is left in the nozzle tip 36, as shown at step 109 in FIG. 5. This predetermined volume is preferably 15 to 20 µl. The final stage (S109) of the blood plasma dispensing step shown in FIG. 5 corresponds to a coating preparing step, in which a small amount of blood plasma component is left to be used for coating.

Figure 6:
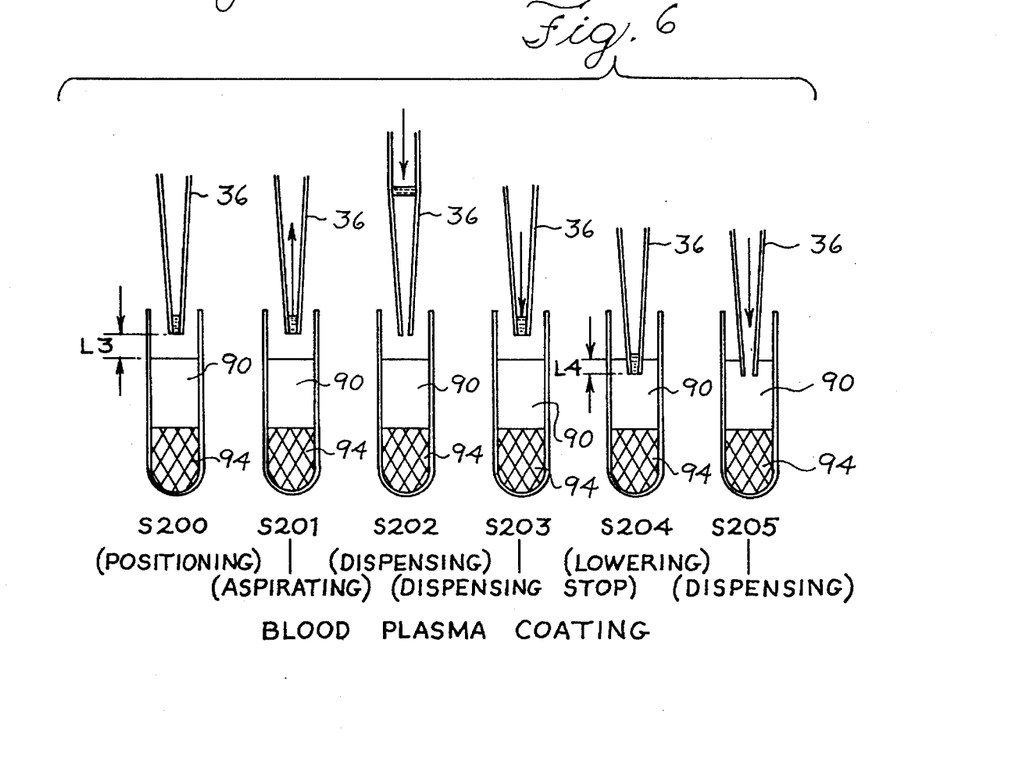
FIG. 6 is an explanatory view for showing a step, in which the inner surface of the nozzle is coated with the blood plasma during a step of pipetting red blood cells.
Figure 7:
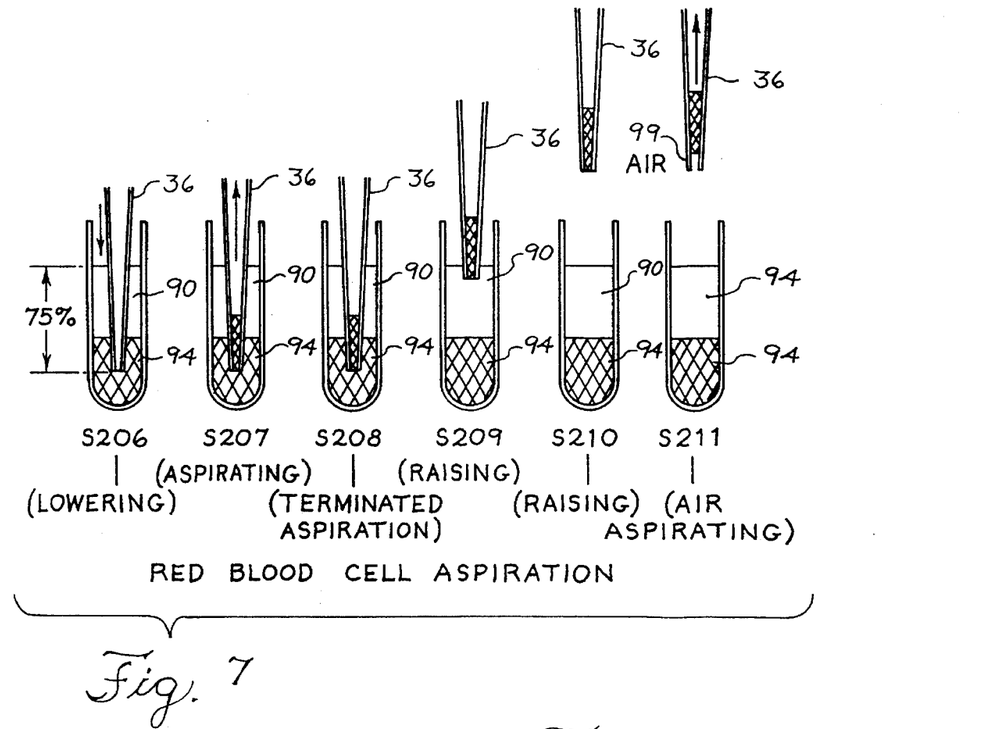
FIG. 7 is an explanatory view for showing a step, in which the red blood cells are aspirated into the nozzle during the step of pipetting the red blood cells.
Figure 8:
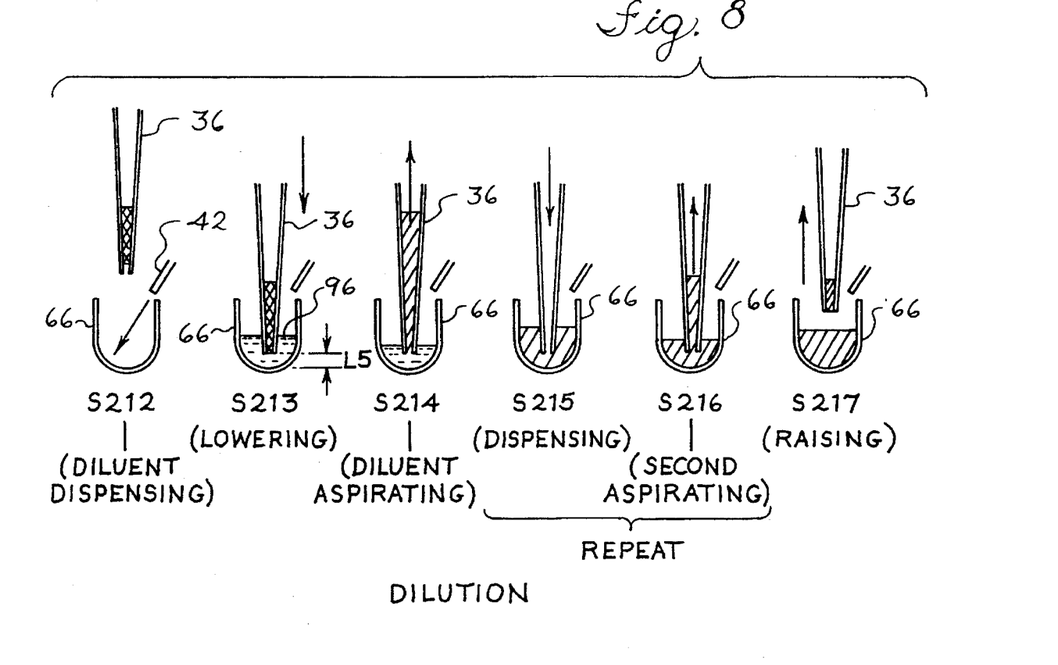
FIG. 8 is an explanatory view for showing a step, in which the red blood cells are diluted during the step of pipetting the red blood cells.
Figure 9:
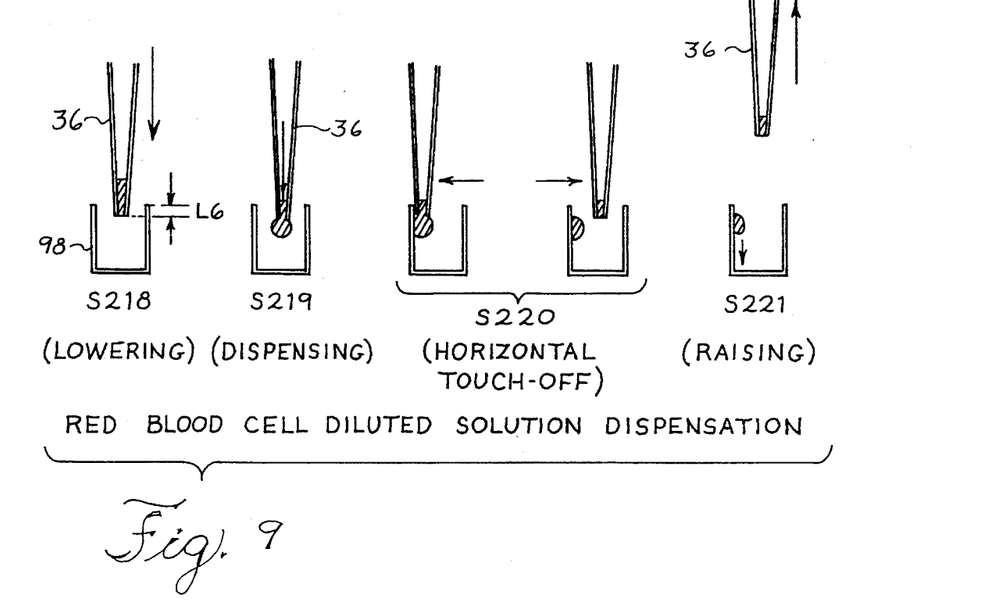
FIG. 9 is an explanatory view for showing a step, in which a red blood cell diluent is dispensed from the nozzle during the step of pipetting the red blood cells.

FIGS. 6 through 9 show the red blood cell pipetting step, which is mainly classified into four steps: a blood plasma coating step of FIG. 6; a red blood cell aspirating step of FIG. 7; a red blood cell diluting step of FIG. 8; and a diluted solution dispensing step of FIG. 9.

Firstly, the blood plasma coating step will now be described with reference to FIG. 6.

After step 109 of FIG. 5. step 200 of FIG. 6 is executed. Namely, by the XYZ robot 34, the nozzle tip 36 is positioned in an upper portion of the test tube 62 from which the blood plasma component has been aspirated at step 102. Specifically, the nozzle tip 36 is positioned so that its distal end is inserted slightly (to be positioned at a distance L3 off the blood surface) into the upper opening of the test tube 62. This positioning would prevent the coating blood plasma from scattering over other blood samples and contaminating them, thus improving the reliability of the apparatus. L3 at step 200 is preferably 5 mm.

In the method of this embodiment, pipetting is performed continuously by using the same nozzle tip 36 throughout the blood plasma pipetting step and the red blood cell pipetting step. Alternatively, at a changing moment between these two steps, the nozzle tip 36 may be exchanged with a new one. In such case, it is necessary to provide a blood plasma component coating step as a preprocessing step before step 200.

At step 201, the coating blood plasma component existing in the nozzle tip 36 is aspirated (raised) again at least to such an extent that the red blood cell component to be subsequently aspirated reaches. Strictly, the coating is executed to such an extent that the red blood cell component diluted afterward, i.e., the diluted solution of red blood cells reaches.

At step 202, the coating blood plasma component is dispensed (lowered), and is stopped when it reaches the distal end of the nozzle tip 36 as shown at step 203 of FIG. 6.

In this embodiment, the coating is accomplished by moving the blood plasma component up and down only one time as shown at step 201 and step 202. Alternatively, the blood plasma component may be moved up and down two or more times, if necessary. However, it is confirmed that moving up and down one time is sufficient for the coating.

At step 204, the nozzle tip 36 is lowered and is stopped when its distal end is inserted into the blood plasma component 90 to be positioned at a distance L4 downward from the blood surface. L4 is preferably 2 to 3 mm. At step 205, the remaining blood plasma component used for coating is returned into the test tube. Thus, in order to use a valuable blood sample without wasting it, the blood plasma component for coating is returned into the test tube. Although only a small amount of blood plasma component is used for coating in this embodiment, a large amount of blood plasma component may be used for coating. If a large amount of blood plasma component is used, it is obliged to aspirate an unnecessarily large amount of blood plasma component at step 102, and at step 205, when returning such large amount of blood plasma component into the tube, there is a risk that the blood plasma component is mixed with the red blood cell component. Consequently, it is preferable that the coating should be done with a small amount of blood plasma component.

After step 205, step 206 of FIG. 7 is executed. At step 206, the nozzle tip 36 is further lowered, so that its distal end is inserted into the red blood cell component 94. At that time it is preferable that the distal end of the nozzle tip 36 is located at a position of about 75% downward from the surface of the blood plasma component, where the whole blood sample is 100%. If the nozzle tip 36 is inserted into the blood plasma component too deeply, a large amount of red blood cell component 94 attaches onto the outer surface of the nozzle tip 36. In contrast, if the nozzle tip 36 is inserted into the blood plasma component too shallowly, it is difficult to aspirate the red blood cell component surely.

At step 207, the red blood cell component 94 is aspirated. In this embodiment, for example, 80 μl of red blood cell component 94 is aspirated.

However, the red blood cell component 94 is a high viscosity liquid or a gel substance, so that considerable pressure and time are needed to aspirate such red blood cell component via the orifice of the distal end of the nozzle tip 36. In this embodiment, the following two ways are used to improve the quickness of aspiration to a maximum extent. In the first way, the inner surface of the nozzle tip 36 is coated with the blood plasma component in order to reduce the frictional resistance of the inner surface of the nozzle tip 36 as much as possible, thus ensuring a smooth aspiration of the red blood cell component. In the second way, an excessively large amount of red blood cell component is aspirated temporarily.

Specifically, the piston 76 of the syringe 46 is drawn to a maximum extent, and thereafter the internal pressure of the air hose 44 is monitored by the pressure sensor 54. When the internal pressure becomes equal to a predetermined value, the piston 76 is returned, so that only a desired amount of red blood cell component is finally aspirated into the nozzle tip 36. That is, a high viscosity solution of red blood cell component cannot be aspirated so as to quickly follow the moving amount of the syringe 46, so initially, the maximum aspiration force is imparted to the nozzle 36, and thereafter, the moving amount of the syringe 46 is returned to a proper value just before a desired amount of red blood cell component is aspirated, thereby obtaining a predetermined amount of aspirated red blood cell component which amount is to be determined by the moving amount of the syringe 46.

At step 208, when a detection value of the pressure sensor becomes substantially equal to an atmospheric pressure, the termination of aspiration is confirmed. Strictly, since the red blood cell component is aspirated into the nozzle tip 36, the internal pressure of the air hose 44 has a tendency to become lower than the atmospheric pressure. Finally at step 208, for example, 80 μl of red blood cell component is aspirated into the nozzle tip 36.

At step 209, the nozzle tip 36 is raised slowly in order to keep the two blood components stable in a separated state and in order to avoid causing any turbulent flow. Near the surface of the blood plasma component 90, the nozzle tip 36 is temporarily stopped from raising as shown in step 209, whereupon the nozzle tip 36 is raised again at step 210.

At step 211, for example, about 10 μl of air is aspirated to provide an air cap 99 at the distal end of the nozzle tip 36. This enables to completely take in the nozzle tip 36 the red blood cell component attaching to an edge of the distal end of the nozzle tip 36, and to prevent the red blood cell component from dropping from the nozzle tip 36.

After step 211, step 212 of FIG. 8 is executed. In the step 212, the nozzle tip 36 is conveyed to an upper position above the diluting container 66, whereupon a predetermined amount of diluent is pipetted into the diluting container 66 through the diluent pipette 42. At step 213, the nozzle tip 36 is lowered from the upper position, so that its distal end is positioned in the diluent 96 at a predetermined distance L5 off the bottom of the diluting container 66. L5 is preferably 2 mm. The diluent may be a physiological salt solution.

At step 214, the diluent 96 is aspirated into the nozzle tip 36. In the conventional method, the red blood cell component was dispensed to be mixed and diluted with the diluent. However, by taking account of the high viscosity and the difficulty of the dispensation of the red blood cell component, the diluent which is easy to be aspirated is previously aspirated, and then the diluent is mixed with the red blood cell component step by step.

At step 215, the mixed solution is dispensed from the nozzle tip 36 into the diluting container 66. At that time, since the red blood cell component is previously diluted by the diluent to a certain degree, the mixed solution can be dispensed extremely easily, compared to the dispensation of a pure red blood cell component. At step 216, the mixed solution, i.e., the diluted solution of red blood cell is aspirated. In this embodiment, step 215 and step 216 are repeated about five times. During the successive steps from step 214, the aspiration or dispensation is initially performed slowly, depending on the viscosity of the substance to be aspirated or dispensed, and thereafter progressively more quickly. At step 214, since the inner surface of the nozzle tip 36 has been previously coated with the blood plasma component, the diluent can be aspirated into the nozzle tip 36 more smoothly than the case in which the inner surface of the nozzle tip 36 is not coated with the blood plasma component.

At step 217, the nozzle tip 36 is stopped temporarily from being raised when its distal end reaches near the liquid surface, and then the nozzle tip 36 is raised again.

After step 217, step 218 of FIG. 9 is executed. The nozzle tip 36 is conveyed to a predetermined well 98 on the microplate by the XYZ robot. The nozzle tip 36 is lowered, so that its distal end is positioned in the well 98 at a predetermined distance L6 downward from the upper opening of the diluting container 66. as shown at step 218. L6 is preferably about 3 mm. Though there is not shown in the drawings, a predetermined amount of reagent has been previously piperred into the individual well 98.

At step 219, a predetermined amount of diluted solution of red blood cell component in the nozzle tip 36 is dispensed, and then a drop of the diluted solution formed at the distal end of the nozzle tip 36 is attached onto the inner surface of the well 98 at step 220. Namely at step 220, by using the horizontal touch-off system, the diluted solution of red blood cell component is dispensed, without bringing the distal end of the nozzle tip 36 into direct contact with the reagent in the lower portion of the well. Thus, contamination is eliminated.

At step 221, the nozzle tip 36 is raised and is then moved to a next well, whereupon the steps from step 218 to step 221 are repeated.

In this embodiment, after the blood plasma pipetting step and the red blood cell pipetting step have been executed for a specific blood sample, the nozzle tip 36 is exchanged with a new one. By using this new nozzle tip, the blood plasma pipetting step and the red blood cell pipetting step are executed in the same way for another blood sample.

The viscosity measuring unit 86 of FIG. 3 will now be described. The viscosity of the red blood cell component is valuable information for diagnosing an illness and is also a valuable material for determining an aspiration pressure to be set when a blood sample is pipetted. In the conventional apparatus, there is not provided any viscosity measuring unit, and the viscosity of a blood sample is measured by a separate measuring instrument. Therefore, after having been subjected to the viscosity measurement, the blood sample has been obliged to be disposed. Further, the viscosity measurement takes a long time and needs a complex operation.

In the apparatus of the present invention, since the control unit 84 is equipped with the viscosity measuring unit 86, it is possible to measure the viscosity of the blood sample while the blood sample being pipetted.

For different viscosities of various liquids, there is an intimate relation between the viscosity and a time from when a predetermined pressure is produced as an initial aspiration pressure, to when the aspiration pressure reaches a certain pressure value. It was confirmed in a simulation that they have a proportional relationship therebetween.

A table 88 represents a relation between a viscosity of a liquid and a time from when the liquid begins to be aspirated under a certain initial aspiration pressure, to when the pressure which returns gradually to an atmospheric pressure reaches a specifically set pressure value.

Specifically, when aspirating the blood sample into the nozzle tip 36, the internal pressure of the air tube 44 is monitored by the pressure sensor 54, and the viscosity measuring unit 86 measures the time from when the piston 76 is drawn to give the initial aspiration pressure, to when the internal pressure of the air tube 44 reaches a predetermined value. The viscosity measuring unit 86 also obtains a viscosity of the blood sample by comparing the measured time with the table 88. The obtained viscosity is indicated on a nonillustrated display unit, and this result is utilized for controlling the syringe 46 by the control unit 84.

There are following advantages from the viscosity measuring unit 86. Since the viscosity can be measured simultaneously with the aspiration of the blood sample, the unit 86 requires no additional time for measuring the viscosity, and realizes a very simple viscosity measurement. Further, it is unnecessary to prepare a separate blood sample only for viscosity measurement.

According to the invention as defined in the claims, since the blood plasma pipetting step includes the blood plasma coating step, and the inner surface of the nozzle tip 36 is coated with the blood plasma component prior to the aspiration of the red blood cell component, it becomes possible to aspirate the high viscosity red blood cell component as smoothly as possible. Therefore the present invention makes it possible to improve the pipetting ability per unit time of the apparatus.

According to the invention as defined in the claims, since the coating blood plasma component is left in the nozzle tip 36 at the end of the blood plasma pipetting step, it is unnecessary to aspirate the coating blood plasma component in an additional step at the beginning of the blood plasma coating step. The blood plasma coating can be performed in a continuous operation.

According to the invention as defined in the claims, since the blood plasma coating can be performed with the nozzle tip 36 positioned in the upper portion of the test tube 62 from which the blood plasma has been taken, another blood sample put in another test tube is prevented from being contaminated with the previous sample. Since the remaining blood plasma used for coating is returned into the test tube, it is possible to perform the blood plasma component coating, without wasting a valuable blood sample, thereby avoiding collecting unnecessary blood sample from a human body.

According to the invention as defined in the claims, since the nozzle tip is a disposable type, it is possible to avoid a labor-intensive and complex operation in thoroughly cleaning the nozzle tip for the next blood sample.

What is claimed is:

1. A method for pipetting a blood sample, wherein a blood plasma component and a red blood cell component vertically separated from each other in a test tube are sequentially pipetted into another recipient containers by a nozzle tip, comprising:

(a) a blood plasma component pipetting step of aspirating the blood plasma existing in an upper portion of the test tube, and transferring the blood plasma component into another recipient container by the nozzle tip;

(b) a red blood cell pipetting step of aspirating the red blood cell component existing in a lower portion of the test tube, and transferring the red blood cell component into another recipient container by the same nozzle tip, (c) said red blood cell pipetting step including a coating step of coating an inner surface of the nozzle tip with the blood plasma component at least to such an extent in the nozzle tip that the red blood cell component to be subsequently aspirated reaches, prior to an aspiration of the red blood cell component.

2. A method according to claim 1, further including a coating preparing step of leaving a small quantity of the blood plasma component to be used for coating, within the nozzle tip at the end of the blood plasma pipetting step.

3. A method according to claim 2, wherein said blood plasma coating step includes:

(a) a positioning step of positioning the nozzle tip containing the blood plasma component to be used for coating in an upper portion of the test tube from which the blood plasma component has been collected;

(b) a step of raising and lowering the blood plasma component, in which a coating blood plasma component is raised and lowered in the nozzle tip, thereby coating an inner face of the nozzle tip therewith, while the nozzle tip is being positioned in the upper portion of the test tube; and (c) a blood plasma returning step of moving the nozzle tip downwardly and then returning the remaining blood plasma into the test tube.

4. A method according to claim 1, wherein the nozzle tip is a disposable type, and the same nozzle tip is used continuously for a single blood sample through both said blood plasma pipetting step and said red blood cell pipetting step, and the nozzle tip is exchanged with a new one prior to pipetting of the next blood sample.

* * * * *